United States Patent
Essenreiter et al.

(10) Patent No.: US 11,210,780 B2
(45) Date of Patent: Dec. 28, 2021

(54) AUTOMATIC IMAGE REGISTRATION OF SCANS FOR IMAGE-GUIDED SURGERY

(71) Applicant: Brainlab AG, Munich (DE)

(72) Inventors: Robert Essenreiter, Munich (DE); Ralf Schwitzko, Holzkirchen (DE); Michael Bertram, Markt Schwaben (DE); Thomas Drexl, Poing (DE); Martin Haimerl, Gilching (DE)

(73) Assignee: Brainlab AG, Munich (DE)

( * ) Notice: Subject to any disclaimer, the term of this patent is extended or adjusted under 35 U.S.C. 154(b) by 202 days.

(21) Appl. No.: 16/305,323

(22) PCT Filed: Aug. 5, 2016

(86) PCT No.: PCT/EP2016/068764
§ 371 (c)(1),
(2) Date: Nov. 28, 2018

(87) PCT Pub. No.: WO2018/024342
PCT Pub. Date: Feb. 8, 2018

(65) Prior Publication Data
US 2020/0286222 A1 Sep. 10, 2020

(51) Int. Cl.
*G06T 7/00* (2017.01)
*A61B 34/10* (2016.01)
(Continued)

(52) U.S. Cl.
CPC .......... *G06T 7/0012* (2013.01); *A61B 34/10* (2016.02); *A61B 34/20* (2016.02); *G06T 7/20* (2013.01);
(Continued)

(58) Field of Classification Search
None
See application file for complete search history.

(56) References Cited

U.S. PATENT DOCUMENTS 6,491,699 B1 * 12/2002 Henderson ............. A61B 90/36
606/130
6,609,022 B2 8/2003 Vilsmeier et al.
(Continued)

FOREIGN PATENT DOCUMENTS

WO 2013192598 A1 12/2013

OTHER PUBLICATIONS

Li, Baojun, and Joseph M. Reinhardt. "Automatic generation of object shape models and their application to tomographic image segmentation." Medical Imaging 2001: Image Processing. vol. 4322. International Society for Optics and Photonics, 2001. (Year: 2001).*

(Continued)

*Primary Examiner* — Samah A Beg
(74) *Attorney, Agent, or Firm* — Tucker Ellis LLP

(57) ABSTRACT

Provided is a method for determining a position of an imaged anatomical body part of a patient. The method includes acquiring patient image data describing a digital image of at least part of a reference device and the anatomical body part, acquiring reference device model data describing a model of at least one of at least one internal surface or at least one external surface of the reference device, determining, —based on the patient image data and the reference device model data, reference device image position data describing a relative position between the reference device and the anatomical body part, acquiring reference device tracking data describing a position of the reference device in the tracking reference system, and determining, based on the reference device image position data and the reference device tracking data, body part tracking data describing a position of the anatomical body part in the tracking reference system.

19 Claims, 6 Drawing Sheets

(51) Int. Cl.
*A61B 34/20* (2016.01)
*G06T 7/73* (2017.01)
*G06T 7/20* (2017.01)

(52) U.S. Cl.
CPC .......... *G06T 7/75* (2017.01); *A61B 2034/102* (2016.02); *A61B 2034/105* (2016.02); *A61B 2034/2051* (2016.02); *A61B 2034/2057* (2016.02); *A61B 2034/2072* (2016.02); *G06T 2207/10072* (2013.01); *G06T 2207/30012* (2013.01); *G06T 2207/30204* (2013.01)

(56) References Cited

U.S. PATENT DOCUMENTS

| | | | |
|---|---|---|---|
| 8,737,708 B2 | 5/2014 | Hartmann et al. | |
| 9,125,624 B2* | 9/2015 | Dekel | A61B 90/39 |
| 2005/0085793 A1* | 4/2005 | Glossop | A61B 90/39 |
| | | | 604/529 |
| 2005/0228266 A1* | 10/2005 | McCombs | A61B 90/39 |
| | | | 600/414 |
| 2011/0098553 A1 | 4/2011 | Robbins et al. | |
| 2012/0289825 A1* | 11/2012 | Rai | A61B 6/463 |
| | | | 600/425 |
| 2013/0322719 A1* | 12/2013 | Dekel | A61B 6/12 |
| | | | 382/131 |
| 2014/0126767 A1* | 5/2014 | Daon | A61B 34/20 |
| | | | 382/103 |
| 2014/0276001 A1* | 9/2014 | Ungi | A61B 90/39 |
| | | | 600/424 |
| 2014/0320600 A1* | 10/2014 | Daon | A61B 34/20 |
| | | | 348/45 |
| 2020/0000523 A1* | 1/2020 | Ferro | A61B 34/10 |

OTHER PUBLICATIONS

Yoshito Otake et al.,"An image-guided femoroplasty system: development and initial cadaver studies"., SPIE—International Society for Optical Engineering. Proceedings Mar. 4, 2010, XP055360020.
European Patent Office, International Search Report and Written Opinion for corresponding PCT application No. PCT/EP2016/068754, dated Jul. 3, 2017, pp. 1-15.

* cited by examiner

AUTOMATIC IMAGE REGISTRATION OF SCANS FOR IMAGE-GUIDED SURGERY

RELATED APPLICATION DATA

This application is a National Phase Application of International Application No. PCT/EP2016/068764 filed Aug. 5, 2016 and published in the English language.

The present invention relates to a computer-implemented method for determining a position of an imaged anatomical body part of a patient in a tracking reference system, a corresponding computer program, a non-transitory program storage medium storing such a program and a computer for executing the program, as well as a system for supporting determining a transformation defining a geometric relationship between a position of an anatomical body part of a patient in an image reference system and a position of the anatomical body part in the tracking reference system, the system comprising an electronic data storage device and the aforementioned computer. Furthermore, the present invention relates to a reference device for use in a navigated medical procedure and use of the reference device.

TECHNICAL BACKGROUND

Currently, automatic registration of an anatomical body part to a tracking reference system is performed by attaching markers to a scanner, calibrating image space relative to the scanner-markers using a calibration phantom and performing registration for use in surgery by registering physical space to the scanner-markers and adding the transformation from there into image space. One approach includes automatic registration by embedding fiducials into a reference device and scanning the reference device. Another approach includes automatic registration by attaching fiducials to the skin of the patient. A third approach includes automatic registration by holding a registration device with embedded fiducials into the scan area and registering it to the dynamic reference. A fourth approach includes automatic registration by attaching a registration device to the patient and attaching a robot to the registration device and to the patient.

All known solutions require an array of fiducials, e.g. image-visible CT- or MR-markers, which are typically metal or glass spheres, rods or other components made of a material with different density than the surrounding material. This applies for registration in x-ray based modalities (CT, Cone-beam-CT, O-Arm, 3D C-arm etc.). For MR, chambers filled with MR-visible liquids are used. These fiducials are typically embedded into a registration device with high accuracy which requires certain manufacturing and assembly efforts. The fiducials may cause artefacts and therefore deteriorate the image quality of the 3D scan. Furthermore, not only the markers but the entire registration device is visible in the scan and distracts the user from the anatomical information.

The present invention is designed to achieve a more reliable method for establishing a positional mapping (a registration) between an image reference system and a tracking reference system used by a navigation system.

The present invention can be used in connection with a system for image-guided surgery such as Spine&Trauma 3D, a product of Brainlab AG.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method encompasses scanning an anatomical body part and first a reference device so that the scan image shows both. A geometric model of the reference device is known, so that the position of the image representation of the reference device in the scan image can be determined by applying a surface match or image fusion algorithm. The reference device is provided with optical markers in a predetermined spatial relationship to those parts of the reference device which are visible in the scanned image. The marker devices are optically tracked so that their position in a tracking reference system is known. Based on the knowledge of the relative position between the markers and the image-visible part of the reference device, a positional transformation between positions in the scan image and positions in the tracking reference system is determined so that, based on the scan image describing the relative position between the image-visible part of the reference device, the position of the anatomical body part in the tracking reference system can be determined. In one example, the method encompasses positioning a second reference device near to the aforementioned (first) reference device. The second reference device is also provided with optical markers so that a relative position between the markers of the first reference device and the markers of the second reference device can be determined by a navigation system suitable for optical tracking. The second reference device may be fixed to the patient so that the first reference device can be removed from the setup once the relative position between the markers of the first reference device and the markers of the second reference device has been established. The position of the anatomical body part in the tracking reference system can then be determined by additionally considering the relative position between the markers of the first reference device and the markers of the second reference device.

General Description of the Present Invention

In this section, a description of the general features of the present invention is given for example by referring to possible embodiments of the invention.

In general, the invention reaches the aforementioned object by providing, in a first aspect, a computer-implemented medical data processing method for determining a position of an imaged anatomical body part of a patient in a tracking reference system. The anatomical body part in one example is at least a part of the patient's spine such as at least a part of a vertebra, but can in other examples be any anatomical body part. The anatomical body part has been imaged by applying a medical imaging modality to the anatomical body part. For example, a digital image has been generated based on the result of the imaging. Imaging the anatomical body part in one general example case takes place before the disclosed method is executed, but may in another example case be part of executing the disclosed method. Likewise, generating the digital image imaging the anatomical body part in one general example case takes place before the disclosed method is executed, but may in another example case be part of executing the disclosed method. The tracking reference system is for example associated with a navigation system usable to conduct an envisaged navigated medical procedure, for example at least part of the navigation system rests in the tracking reference system. Specifically, the anatomical body part is not necessarily defined to rest in the tracking reference system—rather, any motion of the anatomical body part can be described by positional differences between positions of the anatomical body part which are defined in the tracking reference system. The method comprises executing, on at least one processor of at least one computer (for example at least one computer being part of the navigation system), the following exemplary steps which are executed by the at least one processor.

In a (for example first) exemplary step, patient image data is acquired which describes (for example defines and/or represents) a digital image of at least part of a reference device and the anatomical body part. The reference device is a non-anatomical structure and is described in further detail below. The reference device is also called first reference device within this disclosure. In one approach for generating the patient image data, both the anatomical body part and the reference device have been imaged simultaneously by applying a medical imaging modality to the anatomical body part and the reference device. For example, a digital image has been generated based on the result of the imaging. Imaging the anatomical body part and the reference device in one general example case takes place before the disclosed method is executed, but may in another example case be part of executing the disclosed method. Likewise, generating the digital image in one general example case takes place before the disclosed method is executed, but may in another example case be part of executing the disclosed method. The patient image data therefore in one general example is generated before execution of the disclosed method ensues and is then used as an input to the disclosed method. In another example case, generating the patient image data may be part of executing the disclosed method. The patient image data is in one example three-dimensional data (e.g. tomographic image data) and may have been generated by applying at least one of computed x-ray tomography (CT), cone beam CT, magnetic resonance imaging (MR), sonography (ultrasound imaging), positron emission tomography (PET), single-photon emission computed tomography (SPECT) or electron emission tomography (EIT). In another approach for generating the patient image data, the digital image may have been synthesized, for example by generating a synthesized CT or MR from a digital image of the anatomical body part (generated beforehand by applying at least one of the aforementioned imaging modalities) and known constructional data (for example a grid model) describing the physical structure of the reference device. In another example, the patient image data may be two-dimensional data (i.e. defined in exactly two positional dimensions), for example it may be embodied by a digital image generated using a digital imaging device (a camera) operating in the visible wavelength range.

In a further (for example second) exemplary step, reference device model data is acquired which describes (for example defines and/or represents) a model of at least one of at least one internal surface (for example, plane) or at least one external surface of the reference device. An internal surface of the reference device is defined to be a surface lying in the interior of the reference device which represents for example a cut such as a planar (slice) or curved cut through the reference device. In other words, the model of an internal surface is a model of the image appearance (at least one of colour values or inner structure (geometry)) of the reference device on that surface. If a plurality of (specifically, adjacent) internal surfaces are contained in the model, that plurality describes at least a part of the volume of the reference device represented by that set of internal surfaces. A model of at least one external surface includes a model of the image appearance (i.e. at least one of colour values or geometry) of the reference device on a planar or curved exterior (outer, i.e. tangible) surface of the reference device. The reference device model data in one example is three-dimensional data, but in another example be two-dimensional (i.e. defined in exactly two positional dimensions). It is envisaged that the patient image data and the reference device model data have the same dimensionality, i.e. are defined in the same number of positional dimensions. Generally, the patient image data and the device model data are comparable to one another (so that they can be mapped onto one another), i.e. at least the relation between their resolutions and reference systems used to describe positions in both data sets is known, or the resolution or reference systems are at least substantially identical.

The model defines in one example an image appearance of the reference device, i.e. an image representation of the reference device. For example, the model describes a combination of colour values (such as multicolour or greyscale values) defining the appearance of the reference device in a digital image. In one example, the model has been generated based on digital model image data describing at least one image of the reference device. The digital model image data may have been generated applying a tomographic imaging modality to at least part of the reference device. The digital model image data in one example hence is tomographic image data.

In another example, the reference device model data (specifically, the model) describes a three-dimensional structure of the reference device, for example at least one of an internal or a surface structure of the reference device, which is described for example by a geometrical grid. Corresponding information may be available e.g. from predetermined (i.e. already known) construction data for constructing the reference device using computer-aided design.

Generating the reference device model data in one general example case takes place before the disclosed method is executed, but may in another example case be part of executing the disclosed method. In a specific example, the digital model image data may have been generated by combining (for example, by statistically analysing such as averaging) a plurality of images (e.g. tomographic images or two-dimensional, e.g. optical, images) of the same reference device or different reference devices (for example, at least one image or a plurality of images of each reference device), wherein the different reference devices are of the same type (i.e. have the same design). The model may therefore be a statistical image-based model of the reference device.

Thus, the reference device model data may therefore be a volume or outer surface model representing a reference for the image appearance and/or at least one of the external or internal structure (specifically, geometry) of the reference device which may serve as a reference which may be compared to the image representation of the reference device in the patient image data. In this sense, the reference device model data may function as an atlas for the reference device.

In a further (for example third) exemplary step, reference device image position data is determined which describes (for example, defines or represents) a relative position between the reference device and the anatomical body part. The reference device image position data is determined based on the patient image data and the reference device model data. The relative position between the reference device and the anatomical body part is in one example defined in an image reference system in which positions in the digital image described by the patient image data are defined. The image reference system can be used for planning an envisaged medical procedure such as radiotherapy or surgery (e.g. spine surgery). The image reference system is predetermined, e.g. known from the geometry of an imaging device used to generate the patient image data. This serves to determine the position of the image representation of the reference device in the digital image described by the patient image data. The reference device image position data is determined by comparing the model of the reference device to the digital image appearance of the reference device in the digital image described by the patient image data, specifically by searching the digital image described by the patient image data for the image features having at least a predetermined degree of similarity to the image appearance of geometry of the reference device described by the model. This can be done for example by matching the model of the reference device with the digital image described by the patient image data, for example by applying an image fusion or surface matching algorithm to the patient image data and the reference device model data.

In a further (for example fourth) exemplary step, reference device tracking data is acquired which describes (for example, defines or represents) a position of the reference device in the tracking reference system.

The reference device tracking data may in a first example be generated on the basis of electronic signals generated by tracking a (i.e. at least one marker device) attached to or integrally included in the reference device using a tracking system included in the navigation system. Usually, four marker devices are used, which may also be done in the present case, even though a minimum of only three marker devices is required. Using up to six marker devices is usual and may also be done in this case. The marker device may be formed by the reference device itself (e.g. by a base part of the reference device) or comprise at least one marker (for example, a plurality of markers). The spatial relationship (i.e. at least one of position or orientation) between such at least one marker and the reference device is predetermined (i.e. known) and may be used as input to the disclosed method. For example, the marker device may have a plurality of pieces of marker foil material or marker spheres attached to it; the pieces of foil or the marker spheres are in one example reflective (e.g. retroreflective) for at least one infrared or visible light (such markers are called optical markers within this disclosure) so that, if they are illuminated with light of the respective wavelength, the reflections can be received by a detection device such as a stereo camera (which is sensitive in the applicable wavelength range) and transformed into electronic signals, which in turn are then converted into digital data (e.g. using a commonly known analogue-to-digital converter) to generate the reference device tracking data. Alternatively, the marker device may comprise at least one resonant circuit (for example a plurality of resonant circuits) which are subjected to electromagnetic radiation (for example in the wavelength range from 350 Hz to 500 kHz) suitable to generate resonance in the circuits, and the resonance signal is detected by a detection device comprising e.g. an antenna array. Such a marker device is also called an electromagnetic marker device. The detected resonances signals are transformed into electronic signals which are then converted into digital data (e.g. using a commonly known analogue-to-digital converter) to generate the reference device tracking data. In a further alternative example, the marker device may comprise electromagnetically active markers which are electrically powered to emit light (for example, from an emission unit such as a light emitting diode) in the infrared or visible wavelength range, the light then being detected by a detection device such as a stereo camera (which is sensitive in the applicable wavelength range) and transformed into electronic signals, which in turn are then converted into digital data (e.g. using a commonly known analogue-to-digital converter) to generate the reference device tracking data. The relative position between the marker device (marker sphere) and the part of the reference device which is visible in the digital image described by the patient image data is generally predetermined (for example, at least one of known or fixed) and described by for example the reference device model data.

In a second example, the reference device tracking data is determined by analysis of the reference device model data which contains information on the geometry of the reference device (including the marker device) and therefore on the relative position between a base part of the reference device which is identifiable in the digital image described by the patient image data and the position of the marker. That relative position already allows for establishing a transformation between the tracking reference system and the image reference system.

In a further (for example fifth) exemplary step, body part tracking data is determined which describes (for examples, defines or represents) a position of the anatomical body part in the tracking reference system. The body part tracking data is determined based on the reference device image position data and the reference device tracking data. Because the reference device image position data is determined based on the patient image data, the body part tracking data is at least indirectly based on also the patient image data. The body part tracking data is determined based on (specifically, by) determining a transformation between the position of the reference device in the image reference system and the position of the reference device in the tracking reference system. Within the meaning of this disclosure, a transformation is understood to be a linear mapping which may be represented by a matrix and/or matrix multiplication. Such a mapping may be determined by applying basic considerations from linear algebra to the position of the reference device in the image reference system and the position of the reference device in the tracking reference system. Since the relative position between the anatomical body part and the relative to the reference device is defined in the image reference system and is known from the reference device image position data, and the position of the reference device in the tracking reference system is known from the reference device tracking data, a transformation between the tracking reference system and the image reference system (for example, a transformation of bases between the two reference systems) can be established and used for mapping the position of the anatomical body part in the image system to the position of the anatomical body part in the tracking reference system.

In a general case, the relative position between the reference device and the anatomical body part should be unchanged between the point in time at which the patient image data is generated and the point in time at which the reference device tracking data is determined. If this is not the case, a further (second) reference device may be used which has the known (for example unchanged) position relative to the anatomical body part and can be tracked in analogy to the way in which the (first) reference device is tracked (cf. the above description relating to the for example fourth exemplary step of the disclosed method), for example because it is provided with a marker device as described above. Then, the relative position between the first and second marker device can be detected and used as a basis for determining the position of the anatomical body part in the tracking reference system.

In one example, determining the body part tracking data therefore comprises:
  acquiring, at the at least one processor, second reference device tracking data describing a position of the second reference device in the tracking reference system, wherein a relative position between the second reference device and the anatomical body part is predetermined (e.g. at least one of known or fixed)—the second device tracking data is generated for example at the point in time at which the patient image data is generated, and the relative position between the second reference device and the anatomical body part is then kept in the predetermined relationship (for example, kept fixed);
  determining, based on the reference device tracking data and the second reference device tracking data, reference device relative position data describing a relative position between the reference device (i.e. the first reference device) and the second reference device (e.g. by establishing a linear mapping and/or a positional difference vector between the positions of the first and second reference device which have been detected by the tracking in the tracking reference system);
  determining the body part tracking data based on the reference device relative position data, for example by establishing (calculating) a transformation (i.e. a linear mapping and/or positional difference which may be embodied by a vector) between the relative position between the reference devices on the one hand and the relative position between the second reference device and the anatomical body part on the other hand.

In a second aspect, the invention is directed to the reference device, which is usable in a navigated medical procedure.

In examples, the reference device has at least one of the following the properties:
  it is formed in a uniquely orientable manner, for example is provided with an orientation feature which is visible in for example a tomographic image of the reference device (for example, the orientation feature may be recess or a cut having a specific direction and being formed on an outer surface of the reference device which constitutes an easily recognizable image feature in a tomographic image such a CT image of the reference device);
  at least part of it is opaque for x-rays (in this case, the reference device, for example a base part of the reference device, may comprise a high-density plastic material such as PEEK—polyether etherketone or PET—polyethylene terephthalate) or magnetic resonance imaging (in this case, the reference device may comprise a fat-water-marker which is visible in a magnetic resonance image of the reference device);
  it includes a (for example closed) cavity containing gadopentetic acid (for example, Magnevist®);
  at least three optical or electromagnetic markers are attached to it in a predetermined (for example at least one of known or fixed) spatial relationship (for example relative to the reference device and/or to one another);
  it is provided with an attachment means (like a recess in a lateral side of the reference device) for (for example fixedly or non-fixedly) attaching it to a second reference device comprising for example a spine clamp;
  it shows no symmetry at least on its surfaces, i.e. the reference device is asymmetric, for example entirely asymmetric at least concerning its surface appearance and/or surface shape (in this example, the reference device does not display any symmetry according to any possible two- or three-dimensional symmetry group);
  at least one of at least one recess or at least one projection is provided on an external surface (in one example, at only one for example predetermined location on the entire outer surface) of a base part of the reference device (this feature can enhance the precision of determining the position of the reference device in the digital image).

In a third aspect, the invention is directed to use of the reference device according to the preceding claim in a registration procedure for determining a transformation (e.g. a linear mapping) between the image reference system and the tracking reference system, wherein for example the reference device according to the second aspect (the first reference device) is positioned relative to a second reference device for example without establishing a structural connection between the two (first and second) reference devices.

In a fourth aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a fifth aspect, the invention is directed to a non-transitory computer-readable program storage medium on which the program according to the fourth aspect is stored.

In a sixth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer comprises the computer-readable program storage medium according to the fifth aspect.

In a seventh aspect, the invention is directed to a system for supporting determining a transformation defining a geometric relationship between a position of an anatomical body part of a patient in an image reference system and a position of the anatomical body part in a tracking reference system the system comprising:
  a) the at least one computer according to the sixth aspect;
  b) at least one electronic data storage device storing at least the patient image data and the reference device model data; and
  c) a medical imaging device (for example, a tomographic imaging device such as an x-ray computer tomograph, a cone beam CT or a magnetic resonance tomograph, or an ultrasound or an imaging device usable for PET or EIT or SPEC) for taking the patient image data, the medical imaging device being operably coupled to the at least one computer for transmitting a signal to the at least one computer corresponding to the patient image data, wherein the at least one computer is operably coupled to the at least one electronic data storage device for acquiring, from the at least one data storage device, at least one of the patient image data or the reference device model data.

In an example, the system according to the seventh aspect comprises:

d) a marker detection device for detecting the position of at least one optical or electromagnetic marker, wherein the marker detection device is operably coupled to the at least one computer for transmitting a signal to the at least one computer corresponding to the reference device tracking data.

In an eighth aspect, the invention is directed to a system for use in a navigated medical procedure, comprising:

a) the system according to seventh aspect; and
b) the reference device according to second aspect.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to positioning a patient relative to the treatment device for example before any radiotherapy or radiosurgery ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface.

The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

DESCRIPTION OF THE FIGURES

In the following, the invention is described with reference to the appended figures which represent a specific embodiment of the invention. The scope of the invention is however not limited to the specific features disclosed in the context of the figures, wherein

FIG. 1 is a flow diagram illustrating the basic steps of the disclosed method in accordance with the first aspect, which in the illustrative example of FIG. 1 starts with a step S11 of acquiring the patient image data. In subsequent step S12, the reference device model data is acquired, followed by step S13 which encompasses determining the reference device image position data. Then, step S14 acquires the reference device tracking data. Steps S11 to S14 serve as input steps for the last step shown in FIG. 1 which is step S15 encompassing determination of the body part tracking data.

Figure 10:
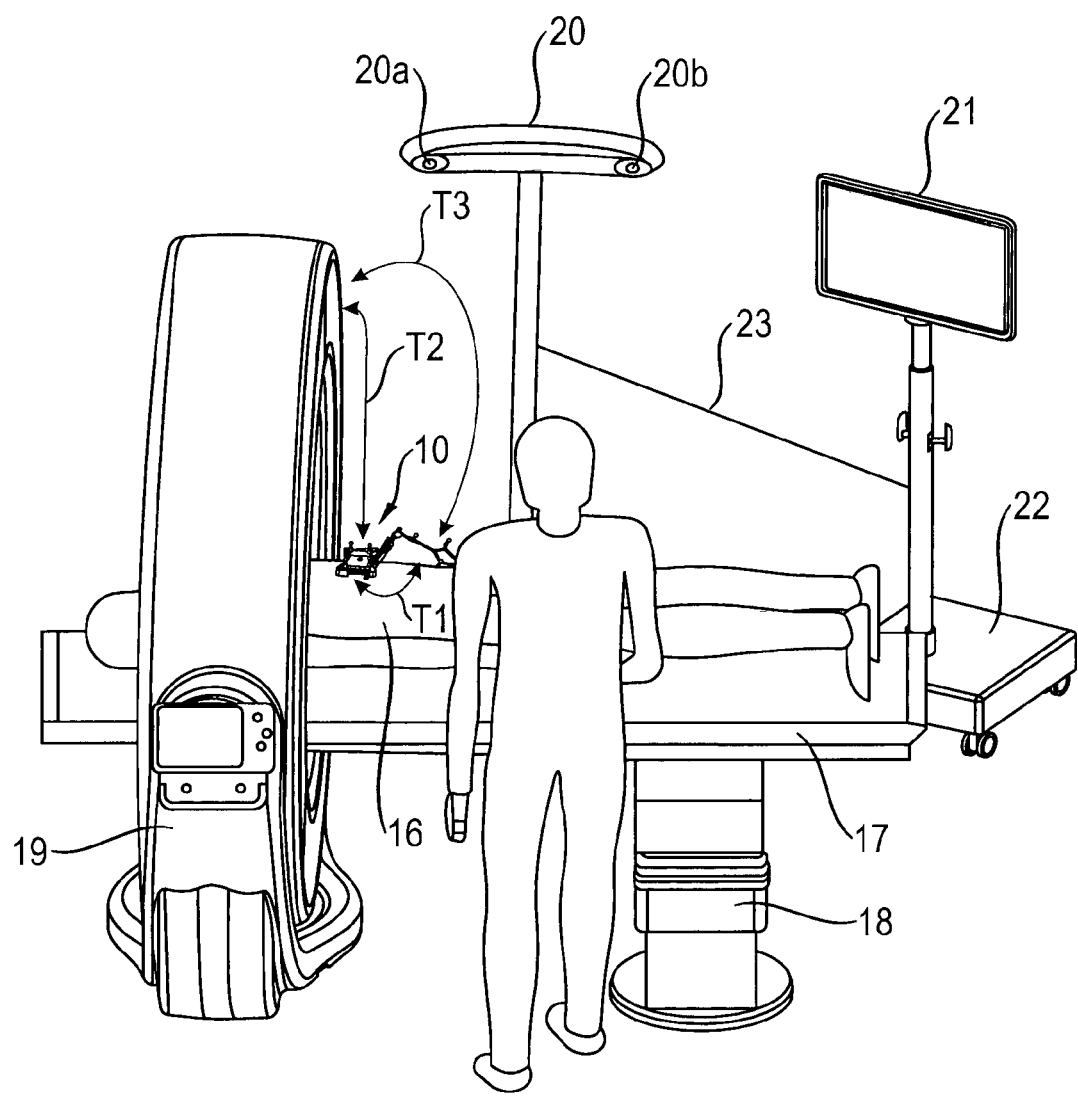
FIG. 10 is a view of setup for treating a patient using the combination of FIG. 9 on a patient in combination with a navigation system.

A specific example of using the setup of FIG. 10 or a setup being technically equivalent to the setup of FIG. 10 comprises the following method steps, which fall into the scope of the method in accordance with the first aspect:

1. The tracking markers of the first reference device are registered to the second reference device (also called dynamic reference) before or after taking the scan for generating the patient image data (resulting in Transformation 1, also abbreviated as T1, the information is included in the reference device tracking data). The dynamic reference defines a physical space for image-guidance of instruments, robots or other devices.
2. Scanning for generation of the patient image data.
3. The data resulting from the scanning (the patient image data) is transferred to the computer of the navigation system.
4. The patient image data is searched (e.g. by the computer of the navigation system) for the image representation of the (first) reference device (also called registration device) and a surface match is performed between known geometric data of the device (the reference device model data) and surface data (describing specifically the external surface) of the first reference device extracted the patient image data. Thereby, the reference device image position data is determined. A transformation from image space (the image reference system) to geometric space of the registration device (the tracking reference system) is performed (resulting in Transformation 2, also abbreviated as T2).
5. The geometry of the first reference device is known from the reference device model data, therefore the transformation from the surface of the first reference device to the tracking markers 12 of the second reference device is known in geometric space of the registration device, i.e. in the tracking reference system (resulting in Transformation 3, also abbreviated as T3).
6. T2+T3 is the transformation from image space ("the scan"), from the image reference system, to the tracking markers of the first reference device, i.e. to the tracking reference system. The transformation from the tracking markers to the second reference device is known as well (as T1), therefore the image reference system can now be registered to tracking reference system e.g. by the software (the corresponding transformation being represented as T1+T2+T3). T1+T2+T3 allows to determine the body part tracking data.

Variants of the sequence are:

First Variant:
1. The position of the first reference device is registered to the position of the second reference device before or after the scan (resulting in Transformation 1, also abbreviated as T1). The positions are defined by the positions of the respective tracking markers and are determined in this example by optical tracking.
2. Scanning, i.e. generating the patient image data.
3. The data resulting from the scanning (the patient image data) is transferred to the computer of the navigation system.
4. The geometry of the registration device is known from the first reference device model data, therefore the transformation from the surface of the first reference device to the tracking markers of the second reference device is known in the tracking reference system (resulting in Transformation 3, also abbreviated as T3).
5. The software searches the patient image data for the representation of the first reference device and performs a surface match between the model of the first reference device and surface data of the device determined in the patient image data. A transformation from the image reference system to the tracking reference system is performed (Transformation 2). Thereby, the reference device image position data is determined.
6. T2+T3 is the transformation from the image reference system to the tracking markers of the first reference device, i.e. the tracking reference system. The transformation from the tracking markers to the second reference device is known as well (as T, the information is included in the reference device tracking data 1), therefore the image reference system can now be registered to the tracking reference system e.g. by the software (the corresponding transformation being represented as T1+T2+T3). T1+T2+T3 allows to determine the body part tracking data.

Second Variant:
1. Scanning, i.e. generating the patient image data.
2. The data resulting from the scanning (the patient image data) is transferred to the computer of the navigation system.
3. The software searches the patient image data for the representation of the first reference device and performs a surface match between the model of the first reference device and surface data of the device determined in the patient image data. A transformation from the image reference system to the tracking reference system is performed (resulting in Transformation 2, also abbreviated as T2). Thereby, the reference device image position data is determined.
4. The geometry of the registration device is known from the first reference device model data, therefore the transformation from the surface of the first reference device to the tracking markers of the second reference device is known in the tracking reference system (resulting in Transformation 3, also abbreviated as T3).

5. The position of the first reference device is registered to the position of the second reference device before or after the scan of step 1 (resulting in Transformation 1, also abbreviated as T1, the information is included in the reference device tracking data). The positions are defined by the positions of the respective tracking markers and are determined in this example by optical tracking.

6. T2+T3 is the transformation from the image reference system to the tracking reference system. The transformation from the tracking markers to the dynamic reference is known as well (as T1), therefore the image space can now be registered to physical space by the software (the corresponding transformation being represented as T1+T2+T3). T1+T2+T3 allows to determine the body part tracking data.

This registration may now be used for image-based guidance of an instrument, a robot or another for example medical device (e.g. microscope such as a microscope usable in a surgical procedure).

In another embodiment, it is also possible to not use the second reference device. Instead, the first reference device needs to have a known, for example fixed, specifically a rigid, connection to the patient. The instrument, robot or other device to be image-guided needs to have a known, for example fixed, specifically a rigid, connection to the registration device or to the patient as well. This embodiment then proceeds as follows:

1. Scanning, i.e. generating the patient image data.
2. The data resulting from the scanning (the patient image data) is transferred to the computer of the navigation system.
3. The patient image data is searched (e.g. by the computer of the navigation system) for the image representation of the (first) reference device (also called registration device) and a surface match is performed between known geometric data of the device (the reference device model data) and surface data (describing specifically the external surface) of the first reference device extracted the patient image data. Thereby, the reference device image position data is determined. A transformation from image space (the image reference system) to geometric space of the registration device (the tracking reference system) is The geometry of the registration device is known from the first reference device model data, therefore the transformation from the surface of the first reference device to the tracking markers of the second reference device is known in the tracking reference system (resulting in Transformation 3, also abbreviated as T3).

5. T2+T3 is the transformation from the image reference system to the tracking markers of the first reference device, i.e. the tracking reference system. The transformation from the tracking markers to the second reference device is known as well (as T1, the information is included in the reference device tracking data), therefore the image reference system can now be registered to the tracking reference system e.g. by the software (the corresponding transformation being represented as T1+T2+T3) for tracking of the instrument, robot or other device in the tracking reference system. T1+T2+T3 also allows to determine the body part tracking data.

The registration can now be used to guide the instrument, robot or other device directly without the need for a dynamic reference.

The above-mentioned surface match comprises the following steps: The surface geometry of the first reference device is known from the reference device model data. A number of points on the surface of the registration device is defined. In the patient image data, a threshold is defined (or calculated) that defines the surface of the representation of the registration device in the patient image data. A complete search over the whole volume, i.e. the whole of the patient image data is performed until a perfect match of the known surface points with the corresponding surface geometry in the patient image data is found. The search over the whole volume can be reduced if the location of the image representation of the first reference device is approximately known before, or by using a rough search before the actual match. With this match, Transformation 2 is determined: the transformation from the image space (image reference system) to the geometric space of the registration device (the tracking reference system).

As an alternative to the surface match described above, an fusion match can be used, which comprises the following steps: From the geometry of the first reference device known from the reference device model data, a synthetic image data set is computed whose coordinate space has a known relation to the geometric space of the registration device (the tracking reference system). This synthetic image data set is fused with the patient image data using suitable similarity measures such as correlations or mutual information. This is done by translating and rotating one data set over the other and calculating the similarity measure for each pose. The pose with the highest similarity is the winning fusion match, i.e. the location of the registration device in the scan data. With this match, Transformation 2 is determined: the transformation from the image space (image reference system) to the geometric space of the registration device (the tracking reference system).

Figure 1:
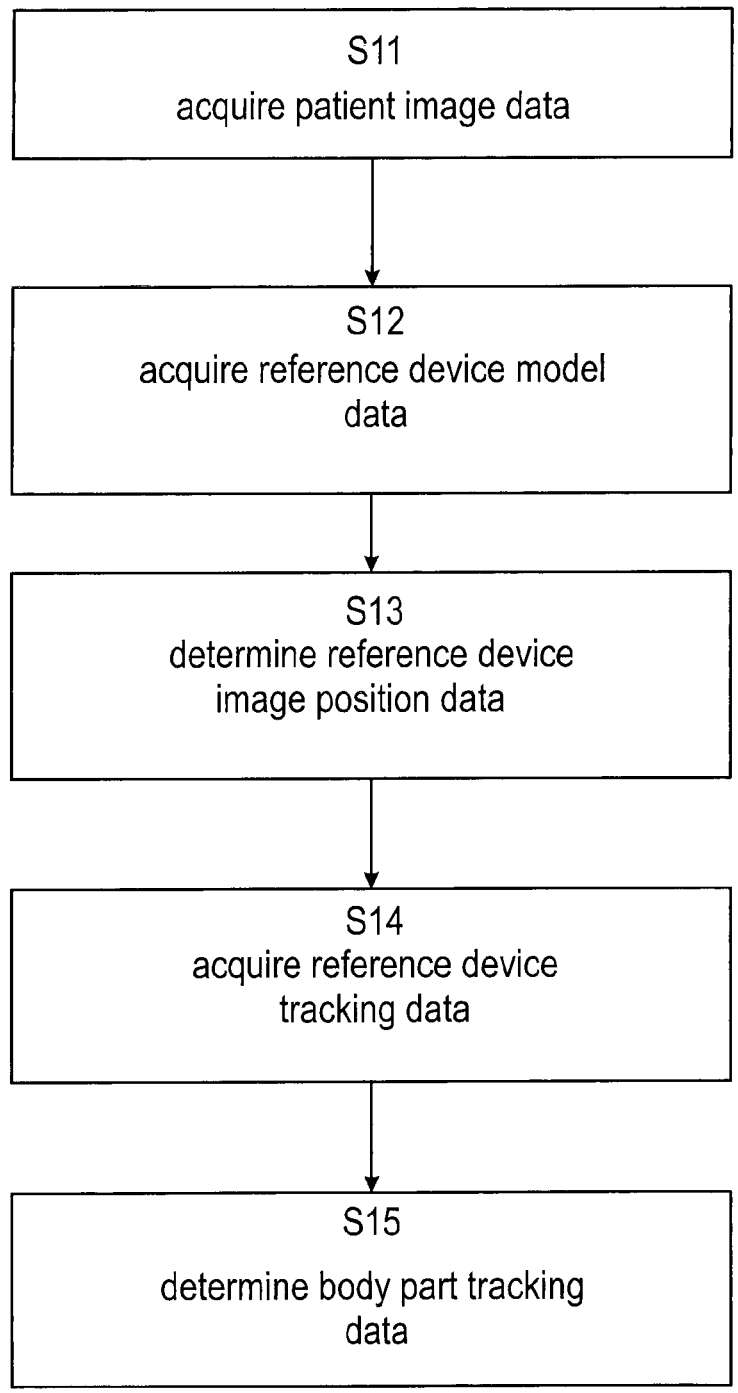
FIG. 1 is a flow diagram showing the basic steps of the disclosed method according to the first aspect.
Figure 2:
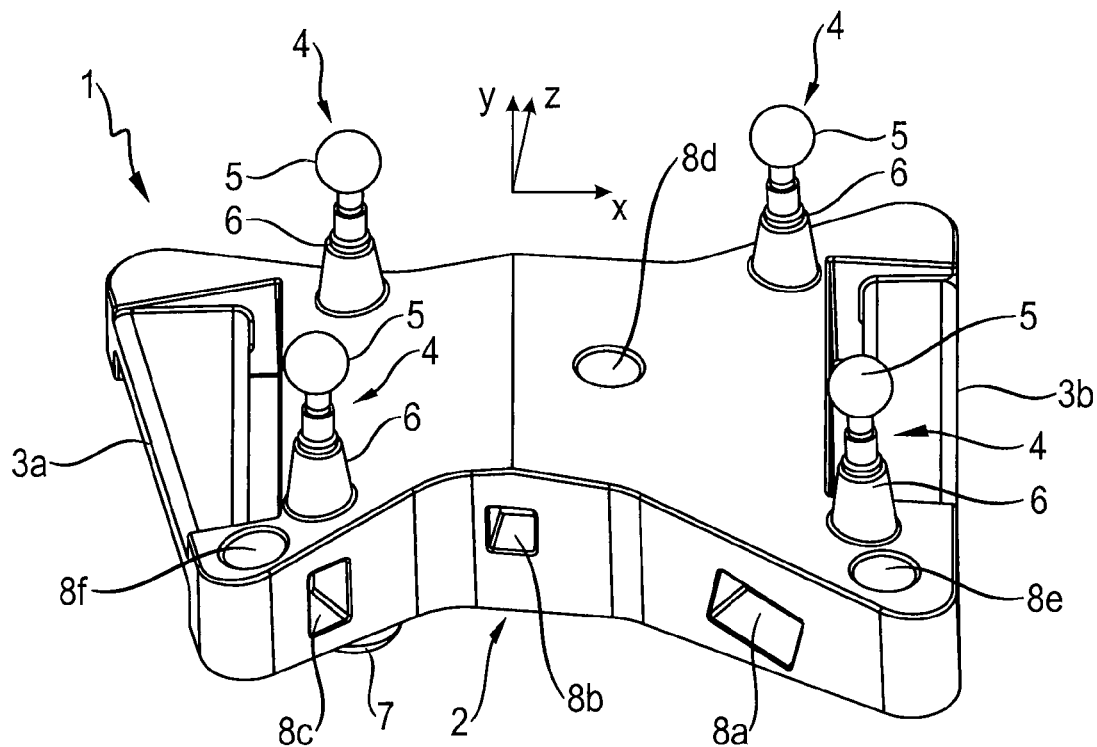
FIG. 2 is a view of the reference device according to the second aspect from an oblique angle.
Figure 3:
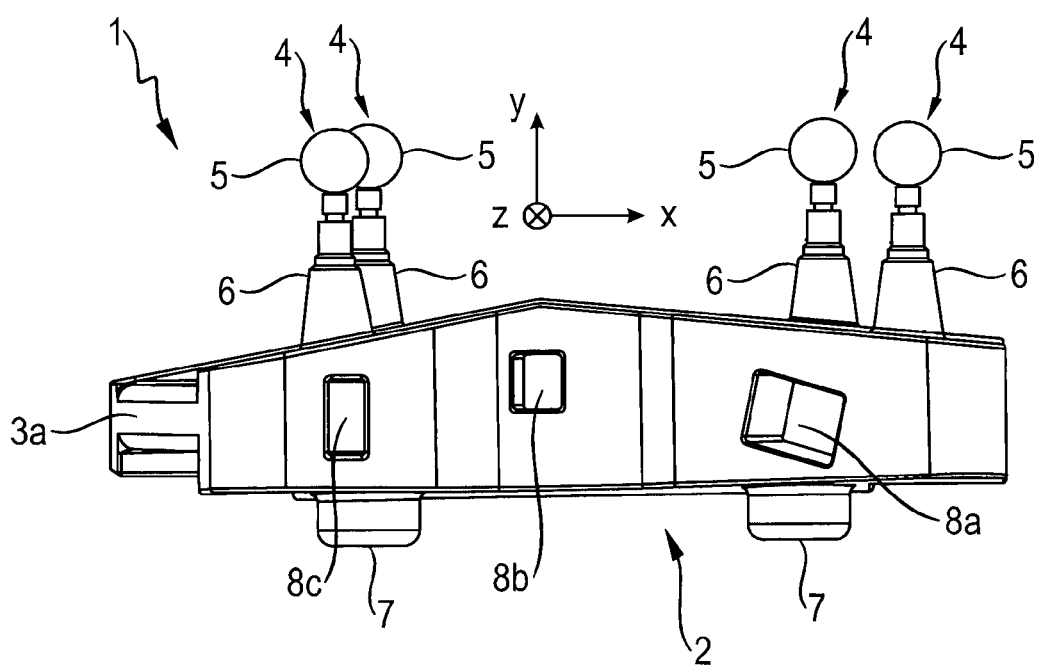
FIG. 3 is a view of the reference device according to the second aspect in a +z-direction.
Figure 4:
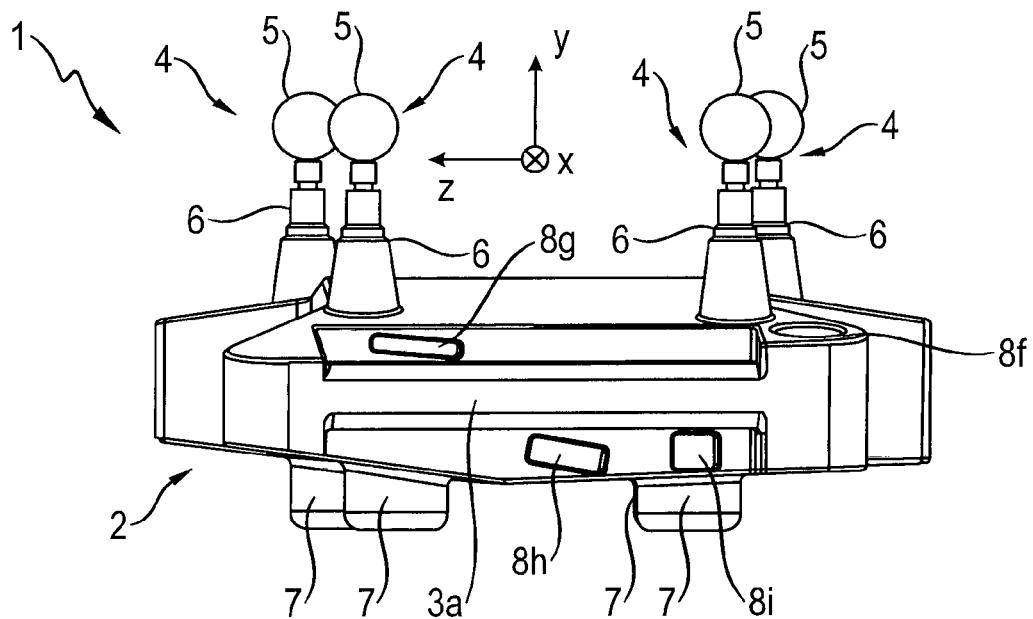
FIG. 4 is a view of the reference device according to the second aspect in a +x-direction direction.
Figure 5:
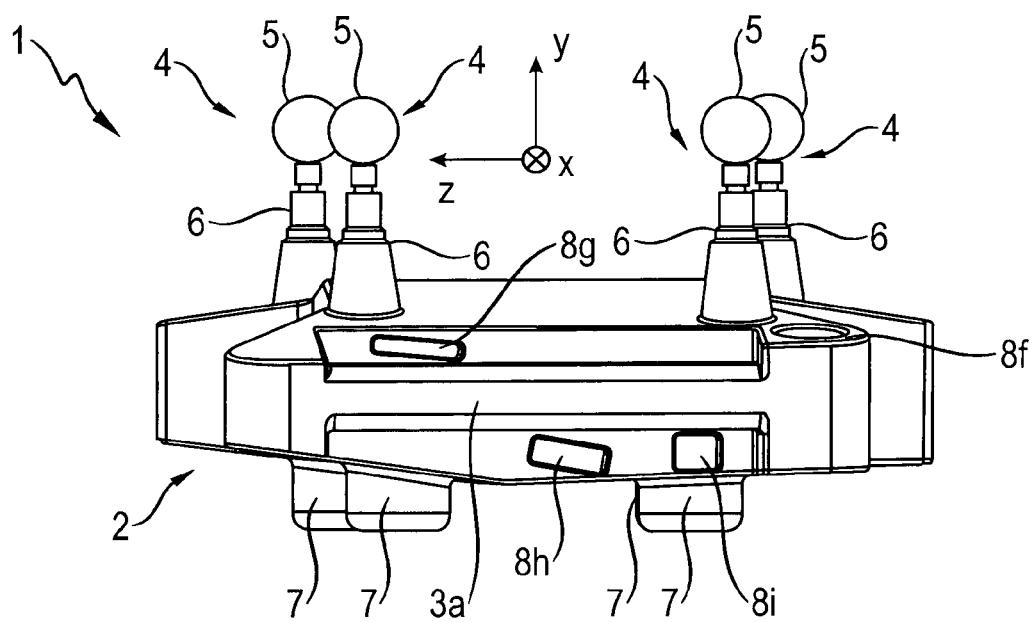
FIG. 5 is a view of the reference device according to the second aspect in a −x-direction.
Figure 6:
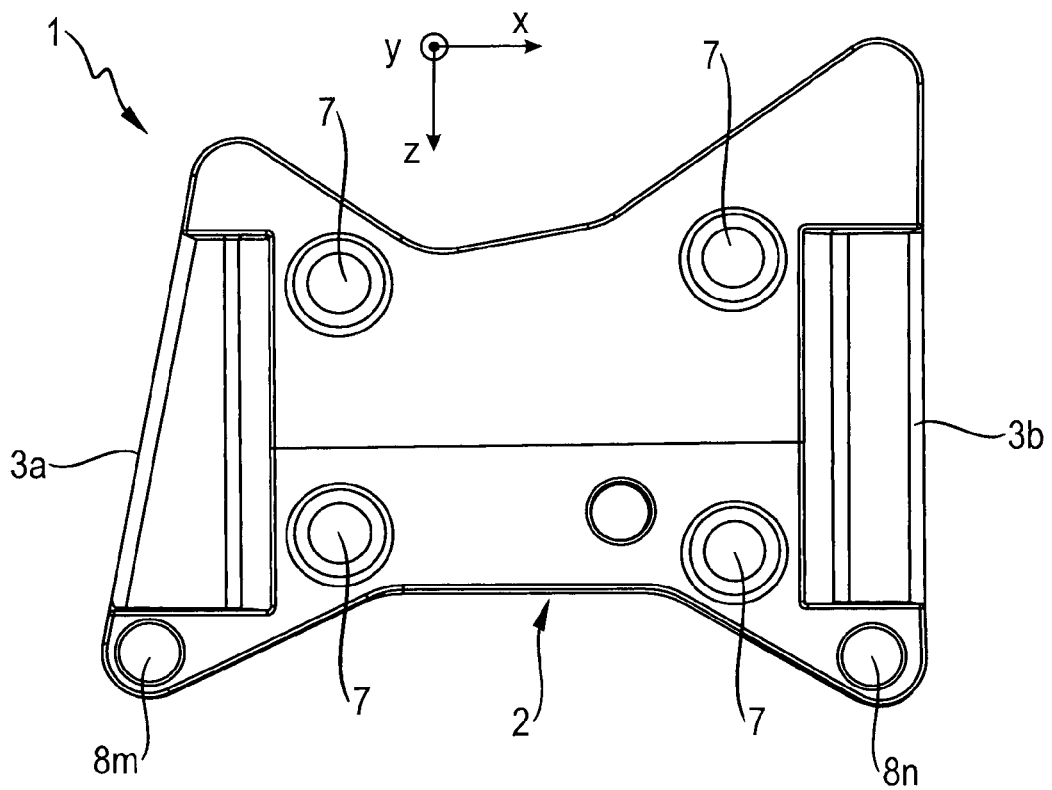
FIG. 6 is a view of the reference device according to the second aspect in a −y-direction.
Figure 7:
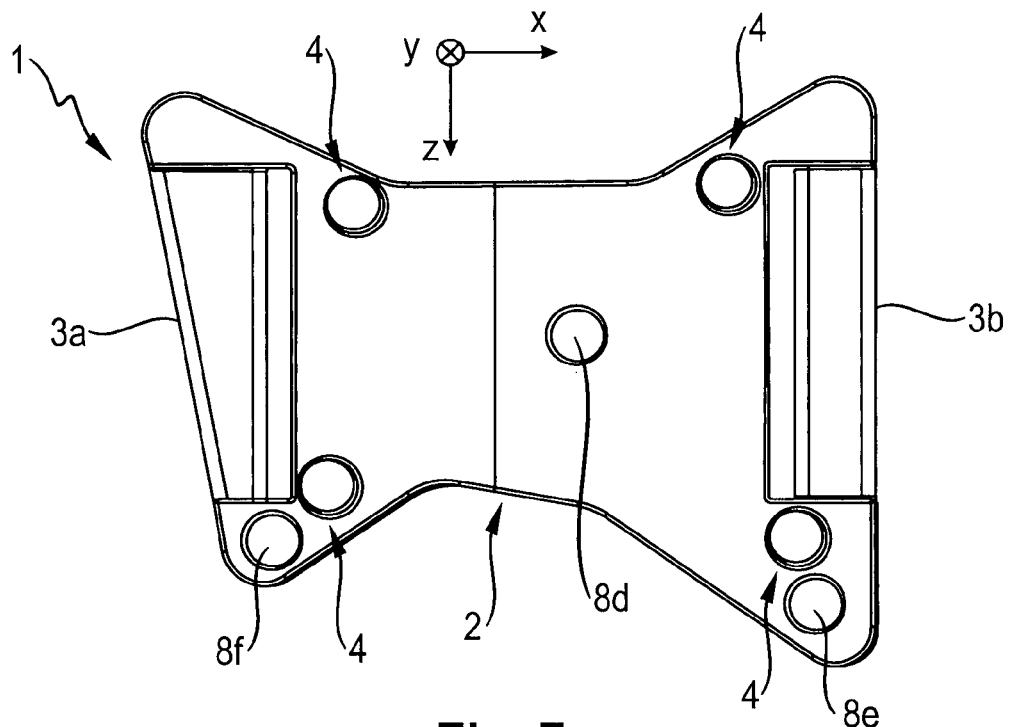
FIG. 7 is a view of the reference device according to the second aspect in a +y-direction.

FIG. 2 shows a view from an oblique perspective onto the first) reference device 1. The first reference device 1 is composed of a block-like base part 2 having handles (for example two handles) 3*a*, 3*b*. The base part 2 has rounded corners in order to avoid injury to the patient e.g. when the block is placed near the anatomical body part. The base part is provided with four markers devices embodied by markers 4 (in the example shown in the figures, on the upper side of the base part 2 which faces the +y-direction of the coordinate system shown in FIGS. 2 to 7), in this case optical markers having a reflective sphere 5 and an attachment part 6 for connection of the reflective sphere 5 with the base part 2. The base part 2 is also provided with four feet 7 for stable placement of the base part onto a surface such as the patient's back. The feet 7 are provided on a lower side of the base part 2 which face the −y-direction of the coordinate system shown in FIGS. 2 to 7).

FIGS. 2 to 7 show different views of the first reference device 1, wherein the same reference signs denote the same features.

As can be seen from FIGS. 2 to 8, reference device 1 has numerous geometric features (also called orientation features) which generate asymmetry of the first reference device 1 in all possible directions:

the lateral surfaces of the base part 2 facing the +x/−x-, +y/−y-, +z/−z-directions have no portion which is parallel to an opposing portion of an opposing lateral surface (i.e. of a lateral surface facing in the x-, y- or z-direction, respectively, having the opposite sign of the direction);

the exterior surface of the base part 2 are provided with an irregular pattern of recesses 8*a*, 8*b*, 8*c*, 8*d*, 8*e*, 8*f*, 8*g*, 8*h*, 8*i*, 8*k*, 8l, 8*m* and 8*n* which displays no two- or three-dimensional symmetry: first of all, the recesses comprise recesses having different geometries (e.g. the circular or cylinder-shaped recesses 8*d*, 8*e*, 8*f*, 8*m* and 8*n*) and the cuboid-shaped recesses 8*a*, 8*b* and 8*c*);

the markers 4 are provided on the upper surface in a positional pattern which does not display any two-dimensional (planar) symmetry (in the plane in which they (i.e. at least the marker spheres 5) are positioned;

the base part 2 should is asymmetric in relation to each of its main axes (i.e. displays no rotational or translational symmetry along any of those axes).

The above of features of the reference device 1 allow to uniquely determine the orientation of the first reference device 1 in a medical image (e.g. in the digital image described by the patient image data) containing an image representation of the first reference device 1. Having a plurality of the recesses 8*a* to 8*n* allows for easier and a more reliable surface matching.

Figure 8:
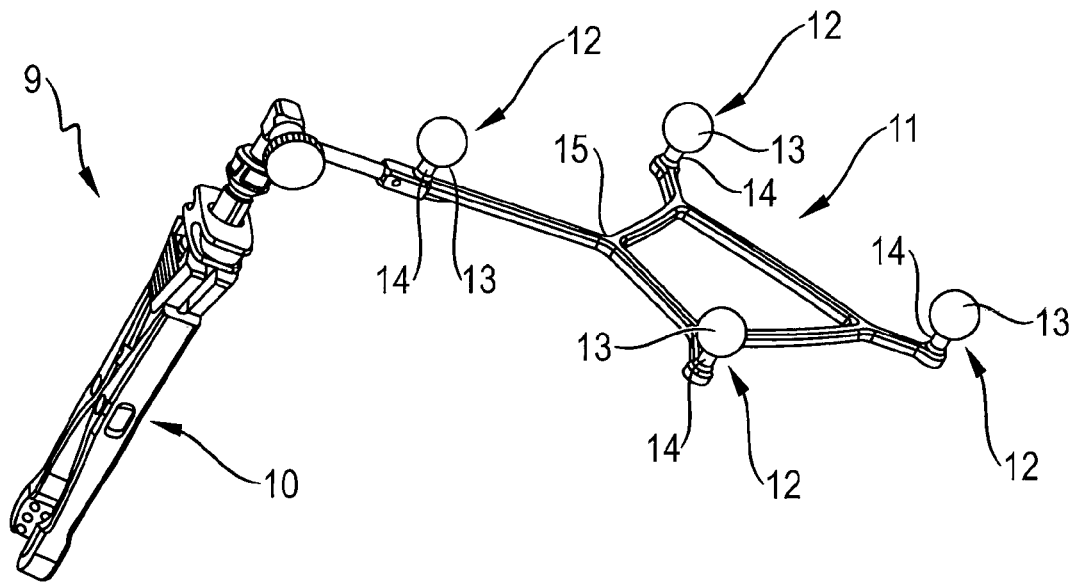
FIG. 8 is a view of a second reference device comprising a spine clamp.

FIG. 8 is an illustration of the second reference device 9 having a clamp 10 (e.g. a spine clamp or a clamp suitable for placement on the exterior of the patient's body without necessitating any surgical activity) and a reference star 11. The reference star is provided on the clamp 10 with an adjustable joint so that the relative position between the clamp 10 and the reference star 11 can be adjusted. The reference star is provided with four reflective marker devices 12 each having an attachment part 14 and a reflective sphere 13. The marker devices are suitable for optical tracking.

Figure 9:
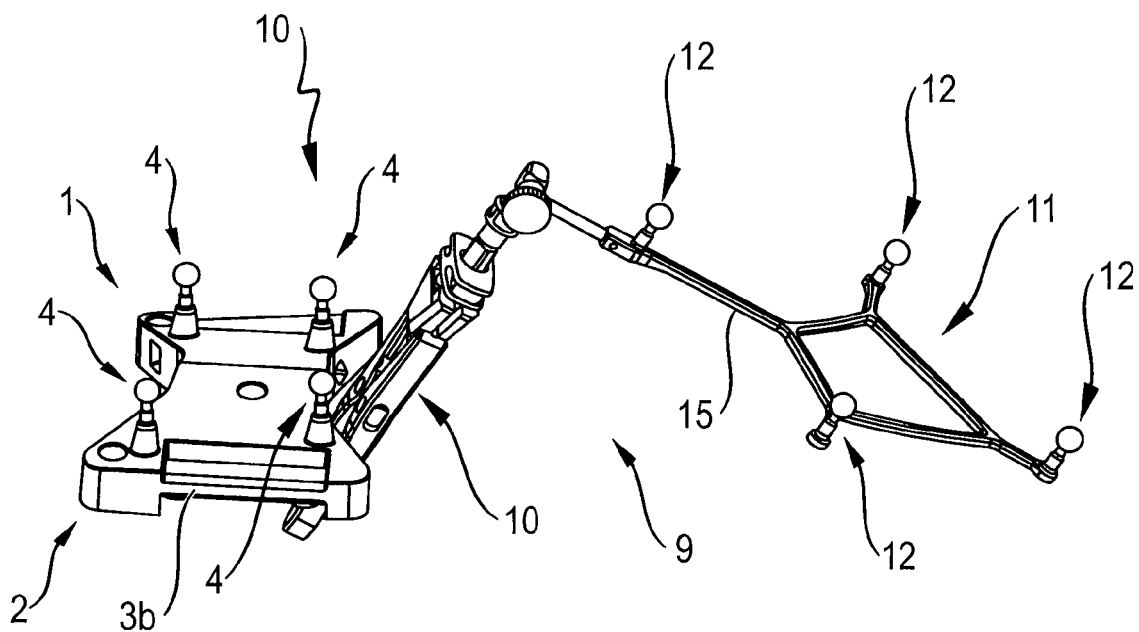
FIG. 9 is an illustration of the reference device according to the second aspect in combination with a second reference.

As shown in FIG. 9, the clamp 10 can be attached to the anatomical body part, for example a patient's vertebra or be clipped onto the exterior of a patient's arm. The first reference device 1 can then be placed near the clamp 10 (in one example, without being fixed to the second reference device 9) to allow for an orientable image representation of the first reference device 1 having a trackable position relative to the second reference device 9 and to thereby allow for establishing a transformation between the image reference system and the tracking reference system. The first reference device 1 and the second reference device 9 then form a system 10 of reference devices.

As shown in FIG. 10, the system 10 of reference devices (specifically, the marker devices 4 and 12) can be tracked during a medical procedure during which the clamp 10 is attached to an anatomical body part belonging to the patient's body 16. The patient image data is generated using an imaging apparatus like a computed x-ray tomograph 19 for imaging the first reference device 1 simultaneously to imaging the anatomical body part so that the digital image described by the patient image data shows both the first reference device 1 and the anatomical body part. The marker devices 4 and 12 are tracked using a navigation system having a marker detection device such as a tracking unit (such as an optical tracking unit, embodied in the example of FIG. 10 by a stereoscopic camera 20 having lenses 20*a* and 20*b*). The tracking unit is operatively coupled (via a wired or wireless data link 23) to a data processing unit 22 (a computer) having a digital processor and a memory and a visual output unit 21 (a display). The tracking unit 20, the data link 23, the computer 22 and the visual output unit 21 for a navigation system. After registration and scanning, the first reference device 1 can be removed from the setup. The patient is then tracked by using only the second reference 9 which has a rigid connection to the patient's body 16 and therefore a fixed position relative to the anatomical body part.

Technical advantages of the disclosed method in accordance with the first aspect and the disclosed reference device in accordance with the second aspect can be outlined as follows:

Using the performance of today's computers, it is possible to register the entire device instead of single fiducials (markers). In former times, fiducials were necessary to speed up calculation time of the registration process. Registering only a few single fiducials (3-10) provided good accuracy at an acceptable calculation time. Today, many points on the surface of the entire device (200-2000) can be used while the calculation time is still acceptable.

Further on, avoiding image-visible, discrete markers has the advantage of better manufacturability of the device. It also avoids deterioration of image quality in the scan because no materials of higher density are required. Eliminating the device from the scan after registration improves usability of the scan data during surgery.

Further on, the inner surfaces of a hollow registration device may be used. With today's manufacturing capabilities (3D-printers), a hollow device with an irregular shape inside can be easily manufactured so that the device might have good properties for cleaning and sterilization but at the same time provide the irregular shape required for a surface match or fusion.

For a fusion match also a registration device that has various 3D areas inside having different densities can be used. The shapes inside as well as the complete shape of the registration device are used for finding a fusion match.

The disclosed method may be summarized as follows:

The outer surface of the first reference device is determined in the scan, a surface match is performed with a model of the first reference device. and image space is registered to physical space. By using the surface of the first reference device, the need for image-visible, discrete markers is avoided. The geometry of the first reference device needs to be of irregular shape, so that as many cross-sections as possible are unique in the image representation of the first reference device in the scan. This way, positional mapping is facilitated.

A second method comprises determining the outer and/or inner shape of the first reference device in the scan, performing a fusion match with a model of the first reference device and registering image space to physical space. By using a fusion match, the need for determining the surface of the device in the scan is avoided.

A sequence of the two above-mentioned methods above may also be used, i.e. first the surface match is performed and then the fusion match is performed for fine adjustment, or vice versa. Only one of the above-mentioned methods is applied.

After registration, the image representation of the first reference device is removed from the scan so that the scan shows only anatomical information.

The invention claimed is:

1. A method for determining a position of an imaged anatomical body part of a patient in a tracking reference system, the method comprising executing, on at least one processor of at least one computer, steps of:

a) acquiring, at the at least one processor, patient image data describing a digital image of at least part of a reference device and the anatomical body part;

b) acquiring, at the at least one processor, reference device model data describing a model of at least one of at least one internal surface or at least one external surface of the reference device;

c) determining, by the at least one processor and based on the patient image data and the reference device model data, reference device image position data describing a relative position between the reference device and the anatomical body part;

d) acquiring, at the at least one processor, reference device tracking data describing a position of the reference device in the tracking reference system;
e) acquiring, at the at least one processor, second reference device tracking data describing a position of a second reference device in the tracking reference system, wherein a relative position between the second reference device and the anatomical body part is predetermined;
f) determining, by the at least one processor and based on the reference device tracking data and the second reference device tracking data, reference device relative position data describing a relative position between the reference device and the second reference device; and
g) determining, by the at least one processor and based on the reference device image position data and the reference device tracking data and the reference device relative position data, body part tracking data describing a position of the anatomical body part in the tracking reference system.

2. The method according to claim 1, wherein the relative position between the reference device and the anatomical body part is defined in an image reference system.

3. The method according to claim 2, wherein the body part tracking data is determined based on determining a transformation between the position of the reference device in the image reference system and the position of the reference device in the tracking reference system.

4. The method according to claim 1, wherein the model defines an image appearance of the reference device.

5. The method according to claim 1, wherein the model has been generated based on digital model image data describing at least one image of the reference device.

6. The method according to claim 5, wherein the digital model image data is tomographic image data.

7. The method according to claim 1, wherein the patient image data and the reference device model data are three-dimensional or two-dimensional data.

8. The method according to claim 1, wherein the patient image data is tomographic image data.

9. The method according to claim 1, wherein the model describes a three-dimensional structure of the reference device.

10. The method according to claim 9, wherein the model describes at least one of an internal or a surface structure of the reference device.

11. The method according to claim 10, wherein the internal or surface structure of the reference device is described by a geometrical grid.

12. The method according to claim 1, wherein the reference device image position data is determined by comparing the model to the digital image appearance of the reference device in the digital image described by the patient image data.

13. The method according to claim 1, wherein the reference device image position data is determined by applying at least one of an image fusion algorithm or a surface match algorithm to the patient image data and the reference device model data.

14. The method according to claim 1, wherein the reference device tracking data has been generated by tracking at least one optical marker or electromagnetic marker having a predetermined spatial relationship relative to the reference device.

15. The method according to claim 14, wherein the at least one optical marker or electromagnetic marker is attached to the reference device.

16. The method according to claim 1, wherein the reference device has at least one of the following properties:
the reference device is provided with an orientation feature which is visible in a tomographic image of the reference device;
at least part of the reference device is opaque for x-rays or magnetic resonance imaging;
the reference device includes a cavity containing gadopentetic acid;
at least three optical or electromagnetic markers are attached to the reference device in a predetermined spatial relationship;
the reference device is provided with an attachment means for attaching the reference device to a second reference device;
at least one of at least one recess or at least one projection is provided on an external surface of a base part of the reference device.

17. A non-transitory computer-readable storage medium having stored thereon computer-executable instructions that, when executed, configure a processor to:
a) acquire, at the at least one processor, patient image data describing a digital image of at least part of a reference device and the anatomical body part;
b) acquire, at the at least one processor, reference device model data describing a model of at least one of at least one internal surface or at least one external surface of the reference device;
c) determine, by the at least one processor and based on the patient image data and the reference device model data, reference device image position data describing a relative position between the reference device and the anatomical body part;
d) acquire, at the at least one processor, reference device tracking data describing a position of the reference device in the tracking reference system;
e) acquire, at the at least one processor, second reference device tracking data describing a position of a second reference device in the tracking reference system, wherein a relative position between the second reference device and the anatomical body part is predetermined acquire, at the at least one processor, second reference device tracking data describing a position of a second reference device in the tracking reference system, wherein a relative position between the second reference device and the anatomical body part is predetermined;
f) determine, by the at least one processor and based on the reference device tracking data and the second reference device tracking data, reference device relative position data describing a relative position between the reference device and the second reference device; and
g) determine, by the at least one processor and based on the reference device image position data and the reference device tracking data and the reference device relative position data, body part tracking data describing a position of the anatomical body part in the tracking reference system.

18. A system for supporting determining a transformation defining a geometric relationship between a position of an anatomical body part of a patient in an image reference system and a position of the anatomical body part in a tracking reference system, the system comprising:

a) at least one electronic data storage device storing at least the patient image data and the reference device model data; and b) a medical imaging device for taking the patient image data, the medical imaging device being operably coupled to at least one processor for transmitting a signal to the at least one processor corresponding to the patient image data, wherein the at least one processor is operably coupled to the at least one electronic data storage device for acquiring, from the at least one data storage device, at least one of the patient image data or the reference device model data, and the at least one processor is further configured to:

a) acquire, at the at least one processor, patient image data describing a digital image of at least part of a reference device and the anatomical body part;

b) acquire, at the at least one processor, reference device model data describing a model of at least one of at least one internal surface or at least one external surface of the reference device;

c) determine, by the at least one processor and based on the patient image data and the reference device model data, reference device image position data describing a relative position between the reference device and the anatomical body part;

d) acquire, at the at least one processor, reference device tracking data describing a position of the reference device in the tracking reference system;

e) acquire at the at least one processor, second reference device tracking data describing a position of a second reference device in the tracking reference system, wherein a relative position between the second reference device and the anatomical body part is predetermined;

f) determine, by the at least one processor and based on the reference device tracking data and the second reference device tracking data, reference device relative position data describing a relative position between the reference device and the second reference device; and g) determine, by the at least one processor and based on the reference device image position data and the reference device tracking data and the reference device relative position data, body part tracking data describing a position of the anatomical body part in the tracking reference system.

19. The system according to claim 18, comprising:

a marker detection device for detecting the position of at least one optical or electromagnetic marker, wherein the marker detection device is operably coupled to the at least one processor for transmitting a signal to the at least one processor corresponding to the reference device tracking data.

* * * * *